(12) United States Patent
Hasegawa et al.

(10) Patent No.: US 7,981,205 B2
(45) Date of Patent: Jul. 19, 2011

(54) DYE COMPOUND AND INK CONTAINING DYE COMPOUND

(75) Inventors: Waka Hasegawa, Kawasaki (JP);
Yasuaki Murai, Kawasaki (JP);
Masashi Hirose, Machida (JP); Takeshi Miyazaki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 276 days.

(21) Appl. No.: 12/432,582

(22) Filed: Apr. 29, 2009

(65) Prior Publication Data

US 2009/0293764 A1 Dec. 3, 2009

(30) Foreign Application Priority Data

Apr. 30, 2008 (JP) ................................. 2008-118803

(51) Int. Cl.
*C09D 11/02* (2006.01)
*C09B 29/36* (2006.01)

(52) U.S. Cl. ..................................... 106/31.48; 534/752
(58) Field of Classification Search ............... 106/31.48; 534/752
See application file for complete search history.

(56) References Cited

U.S. PATENT DOCUMENTS

| 2,432,419 | A | * | 12/1947 | Heimbach | 534/705 |
| 3,420,813 | A | * | 1/1969 | Senn et al. | 534/752 |
| 3,847,919 | A | * | 11/1974 | Knowles et al. | 534/752 |
| 3,980,632 | A | * | 9/1976 | Henzi | 534/610 |
| 4,367,173 | A | * | 1/1983 | Kanter | 534/752 |
| 5,608,041 | A | * | 3/1997 | Schefczik et al. | 534/752 |
| 5,612,465 | A | * | 3/1997 | Schefczik et al. | 534/752 |
| 6,582,502 | B2 | * | 6/2003 | Fujiwara | 106/31.48 |
| 6,723,835 | B1 | * | 4/2004 | Millard et al. | 106/31.48 |
| 6,855,195 | B2 | * | 2/2005 | Nishita et al. | 106/31.48 |
| 7,608,140 | B2 | * | 10/2009 | Link et al. | 106/31.48 |
| 2009/0293765 | A1 | * | 12/2009 | Hasegawa et al. | 106/31.48 |
| 2010/0089285 | A1 | * | 4/2010 | Shintou et al. | 106/31.48 |

FOREIGN PATENT DOCUMENTS

JP 2003-510398 3/2003
* cited by examiner

*Primary Examiner* — Helene Klemanski
(74) *Attorney, Agent, or Firm* — Canon U.S.A., Inc., IP Division

(57) ABSTRACT

A dye compound has the following general formula (1).

General Formula (1)

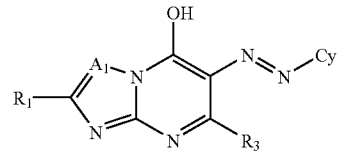

In the general formula (1), $A_1$ denotes N or $CR_2$. When $A_1$ denotes N, $R_1$ denotes an amino group. When $A_1$ denotes $CR_2$, $R_1$ and $R_2$ form an aromatic ring that has an anionic group. $R_3$ denotes an alkyl group, an aryl group, or an aralkyl group. Cy denotes a substituted or unsubstituted aromatic ring.

8 Claims, 2 Drawing Sheets

DYE COMPOUND AND INK CONTAINING DYE COMPOUND

BACKGROUND OF THE INVENTION

1. Field of the Invention

The present invention relates to a dye compound and an ink that contains the dye compound.

2. Description of the Related Art

Although dyes for use in ink jet printing liquids (inks) are generally water-soluble dyes, recorded images that have been printed with inks containing water-soluble dyes can have poor storage stability. More specifically, such dyes can exhibit color fading of images due to sunlight or various illumination lights (i.e., low light resistance), as well as color fading of images due to trace oxidizing gases in the atmosphere (e.g., ozone, $NO_x$, $SO_x$, etc.) (i.e., low gas resistance).

In the interest of providing storage stability, PCT Japanese Translation Patent Publication No. 2003-510398 describes a pyridone azo dye compound as a water-soluble ink jet dye. U.S. Pat. No. 2,432,419 describes an azo hydroxy aza-indolizine dye.

However, the above-described dyes may still fail to provide satisfactory storage stability.

SUMMARY OF THE INVENTION

According to an aspect of the invention, a dye compound is provided having the following general formula (1).

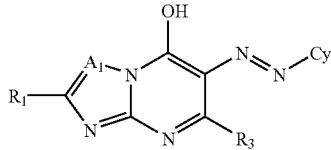

General Formula (1)

In the general formula (1), $A_1$ denotes N or $CR_2$. When $A_1$ denotes N, $R_1$ denotes an amino group. When $A_1$ denotes $CR_2$, $R_1$ and $R_2$ form an aromatic ring that has an anionic group. $R_3$ denotes an alkyl group, an aryl group, or an aralkyl group. Cy denotes a substituted or unsubstituted aromatic ring.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain principles of the present invention.

DESCRIPTION OF THE EMBODIMENTS

Figure 1:
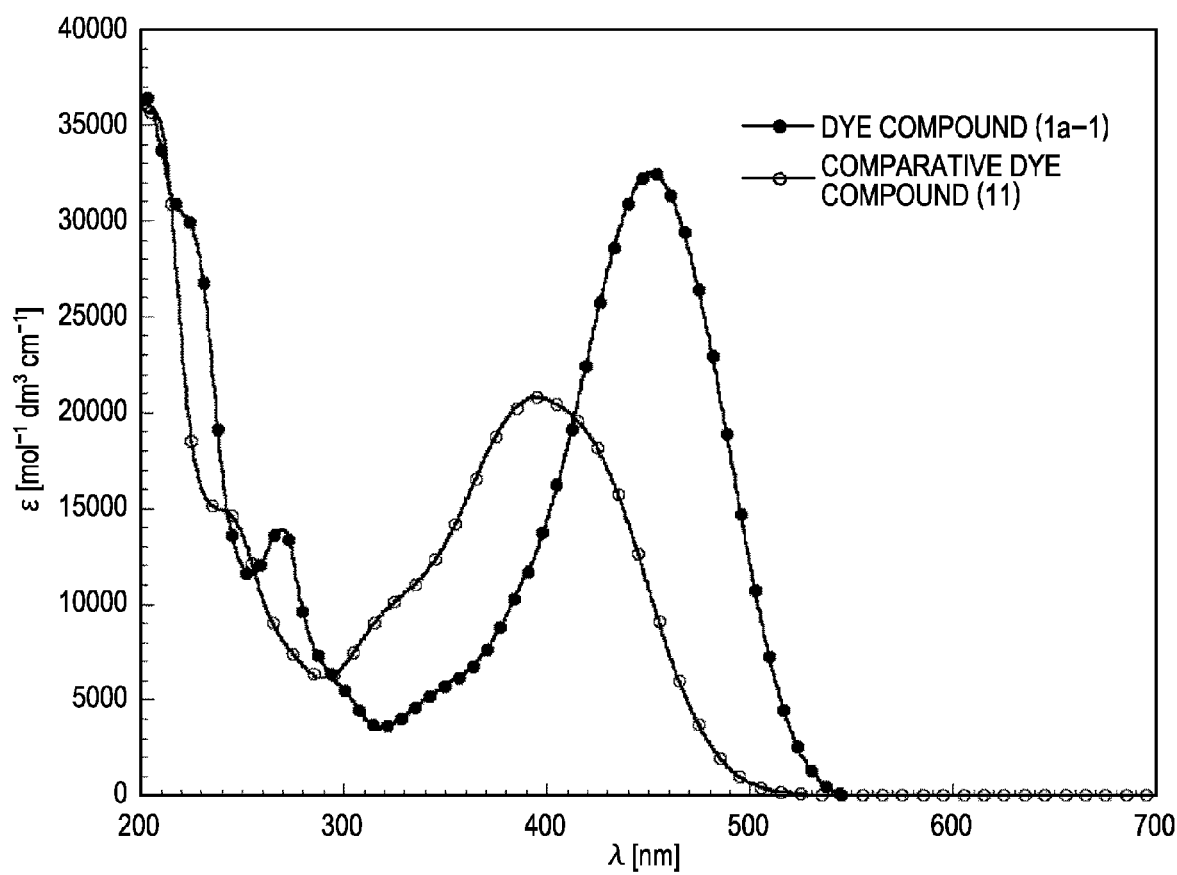
FIG. 1 shows ultraviolet-visible absorption spectra of a dye compound (1a-1) according to an embodiment of the present invention and a comparative dye compound (11) in water at 23° C.

The present invention will be described in detail below by way of embodiments.

The present inventors' investigations have showed that the water-soluble dye described in Japanese Patent Laid-Open (Translation of PCT Application) No. 2003-510398 does not satisfy current weatherproof standards, particularly with regard to light resistance. The azo hydroxy aza-indolizine dye described in U.S. Pat. No. 2,432,419 also does not satisfy the current weatherproof standards, particularly with regard to gas resistance. Furthermore, inks that contain these dyes may have low storage stability.

As a result of diligent investigations to solve problems of the related art, the present inventors have found that a dye compound having the following general formula (1) may be capable of forming images having relatively high light resistance and gas resistance. The present inventors have also found that a dye compound having the following general formula (1) may be capable of being used as a coloring material for an ink to provide an ink having relatively high storage stability.

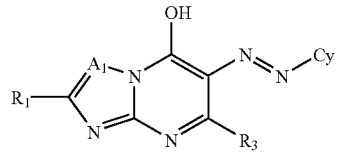

General Formula (1)

In the general formula (1), $A_1$ denotes N or $CR_2$. When $A_1$ denotes N, $R_1$ denotes an amino group. When $A_1$ denotes $CR_2$, $R_1$ and $R_2$ form an aromatic ring that has an anionic group. $R_3$ denotes an alkyl group, an aryl group, or an aralkyl group. Cy denotes a substituted or unsubstituted aromatic ring.

An embodiment of a dye compound having the general formula (1) will be described in detail below.

In the general formula (1), $A_1$ denotes N or $CR_2$. When $A_1$ denotes N, $R_1$ denotes an amino group. When $A_1$ is N and $R_1$ is an amino group, a solution of a dye compound having the general formula (1) may have improved storage stability. The amino group may also have at least one substituent that does not significantly reduce the water solubility and storage stability of a dye compound according to aspects of the present invention. Examples of the substituent may include, but are not limited to, alkyl groups, such as methyl, ethyl, n-propyl, isopropyl, n-butyl, isobutyl, sec-butyl, and tert-butyl, aryl groups, such as phenyl and naphthyl, aralkyl groups, such as benzyl, acyl groups, such as acetyl and benzoyl, a mesyl group, a p-toluenesulfonyl group, a carbamoyl group, a sulfamoyl group, a triazinyl group, and a benzothiazolyl group. The amino group may be, for example, an unsubstituted amino group, an N-methylamino group, an N-ethylamino group, an N-benzylamino group, an N,N-dimethylamino group, an N,N-diethylamino group, an N-acetylamino group, or an N-triazinylamino group. These amino groups may be relatively easy to synthesize, and can impart relatively high water solubility to the dye compound. When $A_1$ denotes $CR_2$, $R_1$ and $R_2$ form an aromatic ring that has an anionic group. Examples of the anionic group may include, but are not limited to, a carboxylic acid group, a sulfonic acid group, and a phosphoric acid group, as well as their ionized forms and their salts with counter ions. The counter ions can include, for example, one or more of alkali metal ions, such as at least one of lithium, sodium, and potassium ions, and ammonium ions, such as at least one of methylammonium, dimethylammonium, trimethylammonium, tetramethylammonium, ethylammonium, diethylammonium, triethylammonium, tetraethylammonium, n-propylammonium, isopropylammonium, diisopropylammonium, n-butylammonium, tetra-n-butylammonium, isobutylammonium, monoethanolammonium, diethanolammonium, and triethanolammonium ions. In one embodiment, the anionic group may be a sulfonic acid group to increase the water solubility of a dye compound and improve the storage stability of an ink.

such as a five-membered nitrogen-containing heteroaromatic ring, to improve the light resistance of a dye compound.

A dye compound having the general formula (1) according to aspects of the present invention further has tautomers, one of which has the following general formula (1'). A dye compound according to the present invention, including these tautomers, is expressed by the general formula (1).

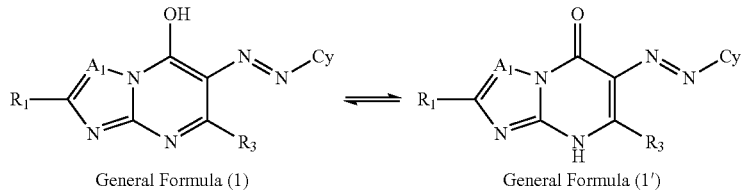

General Formula (1)          General Formula (1')

$R_3$ in the general formula (1) denotes an alkyl group, such as for example a methyl, ethyl, n-propyl, isopropyl, n-butyl, isobutyl, sec-butyl, or tert-butyl group, an aryl group, such as for example a phenyl or naphthyl group, or an aralkyl group, such as for example a benzyl or phenethyl group. $R_3$ may also have a substituent. Examples of the substituent can include, but are not limited to, halogen atoms, such as fluorine, chlorine, bromine, and iodine, and alkoxy groups, such as methoxy, ethoxy, n-propoxy, and isopropoxy. Among others, when $R_3$ is a methyl group, a dye compound having the general formula (1) may be synthesized relatively easily.

According to one embodiment, a dye compound having the general formula (1) according to aspects of the present invention may be a dye compound having a general formula (2), which may also be highly soluble in an aqueous medium.

General Formula (2)

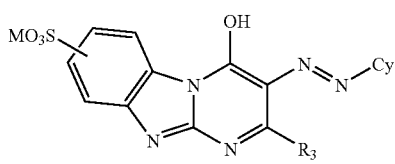

In the general formula (2), $R_3$ denotes an alkyl group, an aryl group, or an aralkyl group. Cy denotes a substituted or unsubstituted aromatic ring. M denotes a hydrogen atom or a counter ion.

Cy in the general formula (1) or the general formula (2) according to the present invention denotes a substituted or unsubstituted aromatic ring. Examples of the aromatic ring may include, but are not limited to, aromatic carbocyclic groups, such as phenyl and naphthyl, and heteroaromatic ring groups, such as imidazolyl, thiazolyl, oxazolyl, pyrrolyl, oxadiazolyl, thiadiazolyl, pyrazolyl, 1,2,3-triazolyl, 1,2,4-triazolyl, furyl, thienyl, pyridyl, pyrimidinyl, pyrazinyl, pyridazinyl, benzimidazolyl, and benzothiazolyl. The aromatic ring may also optionally be substituted with one or more of an alkyl group, a carboxylic acid group, and a sulfonic acid group. In one version, the aromatic ring may be substituted with a carboxylic acid group or a sulfonic acid group to improve the solubility of a dye compound in an aqueous medium. The carboxylic acid group or the sulfonic acid group in Cy may further be adjacent to an azo group, to improve the gas resistance of a dye compound. Furthermore, in one version, Cy may be a nitrogen-containing heteroaromatic ring, In the general formula (1'), $A_1$ denotes N or $CR_2$. When $A_1$ denotes N, $R_1$ denotes an amino group. When $A_1$ denotes $CR_2$, $R_1$ and $R_2$ form an aromatic ring that has an anionic group. $R_3$ denotes an alkyl group, an aryl group, or an aralkyl group. Cy denotes a substituted or unsubstituted aromatic ring.

An example of a method for manufacturing a dye compound having the general formula (1) according to aspects of the present invention will be described below. A method for manufacturing a dye compound having the general formula (1) according to aspects of the present invention may include the following two steps. In a first step, an aromatic amine compound having the following general formula (3) is condensed with a compound having the following general formula (4) in the presence or absence of a solvent, to produce a compound having the following general formula (5). An appropriate condensing agent may be used in the condensation reaction.

General Formula (3)

In the general formula (3), $A_1$ denotes N or $CR_2$. When $A_1$ denotes N, $R_1$ denotes an amino group. When $A_1$ denotes $CR_2$, $R_1$ and $R_2$ form an aromatic ring that has an anionic group.

General Formula (4)

In the general formula (4), $R_3$ denotes an alkyl group, an aryl group, or an aralkyl group. $R_4$ denotes an alkyl group.

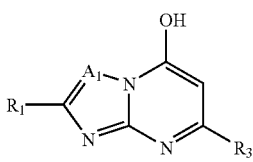

General Formula (5)

In the general formula (5), $A_1$ denotes N or $CR_2$. When $A_1$ denotes N, $R_1$, denotes an amino group. When $A_1$ denotes $CR_2$, $R_1$ and $R_2$ form an aromatic ring that has an anionic group. $R_3$ denotes an alkyl group, an aryl group, or an aralkyl group.

In a second step, the compound having the general formula (5) produced in the first step is coupled with a diazo group of an aniline derivative having the following general formula (6) to produce a dye compound having the general formula (1).

Cy—$NH_2$            General Formula (6)

In the general formula (6), Cy denotes a substituted or unsubstituted aromatic ring.

In the condensation reaction in the first step, the aromatic amine compound having the general formula (3) and the compound having the general formula (4) may be heated under reflux in the absence of solvent or in the presence of methanol, ethanol, glacial acetic acid, or mixed solvent thereof to produce the compound having the general formula (5). The amount of the mixed solvent may generally be, but is not limited to, not more than 100 times by mass the amount of the aromatic amine compound having the general formula (3). An appropriate condensing agent may be used in the condensation reaction. Examples of the condensing agent include, but are not limited to, sodium alkoxide, piperidine, triethylamine, and N,N-dimethylaniline.

The coupling reaction in the second step may be performed by a known coupling method. More specifically, the compound having the general formula (5) may be coupled with the diazo group of the aniline derivative having the general formula (6) to produce the dye compound having the general formula (1). An example of a specific coupling method may be as follows. First, the aniline derivative having the general formula (6) is reacted with a nitrite, such as sodium nitrite, in a water medium in the presence of an inorganic acid, such as hydrochloric acid or sulfuric acid, to produce a corresponding diazonium salt. The diazonium salt is then coupled with the compound having the general formula (5) to produce the dye compound having the general formula (1).

The end product resulting from these steps may be treated by an aftertreatment method suitable for organic synthesis reactions, and may further be purified before use in its intended application.

$R_3$ and Cy in the general formula (2), $A_1$, $R_1$, $R_3$, and Cy in the general formula (1'), $A_1$ and $R_1$ in the general formula (3), $R_3$ in the general formula (4), $A_1$, $R_1$, and $R_3$ in the general formula (5), and Cy in the general formula (6) denote the same components as in the general formula (1).

A dye compound having the general formula (1) can be produced by the manufacturing method described above. The following are specific examples of a dye compound having the general formula (1) according to aspects of the present invention. However, the present invention is not limited to these examples.

TABLE 1

General Formula (1a)

| Compound No. | $R_3$ | $R_4$ | $R_5, R_6$ | $R_7$ | Cy |
|---|---|---|---|---|---|
| 1a-1 | —$CH_3$ | —H | One is —$SO_3Na$ and the other is —H | —H | (structure with $SO_3Na$ and $C(O)ONa$) |
| 1a-2 | —$CH_2CH_3$ | —H | One is —$SO_3Na$ and the other is —H | —H | (structure with $SO_3Na$ and $C(O)ONa$) |
| 1a-3 | (phenyl) | —H | One is —$SO_3Na$ and the other is —H | —H | (structure with $SO_3Na$ and $C(O)ONa$) |

TABLE 1-continued

General Formula (1a)

| Compound No. | R$_3$ | R$_4$ | R$_5$, R$_6$ | R$_7$ | Cy |
|---|---|---|---|---|---|
| 1a-4 | —CH$_2$—C$_6$H$_5$ (benzyl) | —H | One is —SO$_3$Na and the other is —H | —H | 2-methyl-5-sulfo-benzoate (Na salts): methylbenzene with SO$_3$Na and C(O)ONa substituents |
| 1a-5 | —CH$_3$ | —H | One is —COONa and the other is —H | —H | 2-methyl-5-sulfo-benzoate (Na salts) |
| 1a-6 | —CH$_3$ | —H | One is —SO$_3$Na and the other is —H | —H | 2-methyl-benzothiazole-6-sulfonate Na |
| 1a-7 | —CH$_3$ | —H | One is —SO$_3$Na and the other is —H | —H | 3,5-dimethyl-1-(3-sulfophenyl)pyrazole Na |
| 1a-8 | —CH$_3$ | —H | One is —SO$_3$Na and the other is —H | —H | 3-methylpyridine-2-carboxylate Na |
| 1a-9 | —CH$_3$ | —H | One is —SO$_3$Na and the other is —H | —H | sodium 2-methylbenzoate |
| 1a-10 | —CH$_3$ | —H | One is —SO$_3$Na and the other is —H | —H | sodium 3-methylbenzoate |

TABLE 1-continued

General Formula (1a)

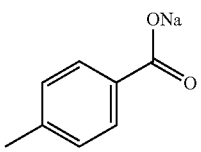

| Compound No. | R₃ | R₄ | R₅, R₆ | R₇ | Cy |
|---|---|---|---|---|---|
| 1a-11 | —CH₃ | —H | One is —SO₃Na and the other is —H | —H | (4-methylbenzoate, ONa) |

TABLE 2

General Formula (1b)

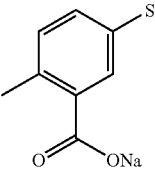

| Compound No. | R₁ | R₃ | Cy |
|---|---|---|---|
| 1b-1 | —NH₂ | —CH₃ | (2-methyl-5-sulfonato-benzoate disodium) |
| 1b-2 | —NH₂ | —CH₂CH₃ | (2-methyl-5-sulfonato-benzoate disodium) |
| 1b-3 | —NH₂ | (4-methylphenyl) | (2-methyl-5-sulfonato-benzoate disodium) |
| 1b-4 | —NH₂ | (benzyl, —CH₂—Ph) | (2-methyl-5-sulfonato-benzoate disodium) |
| 1b-5 | —NH₂ | —CH₃ | (2-methylbenzothiazole-6-sulfonate Na) |

TABLE 2-continued

General Formula (1b)

| Compound No. | R₁ | R₃ | Cy |
|---|---|---|---|
| 1b-6 | —NH₂ | —CH₃ | 3,5-dimethyl-1-(3-sulfonatophenyl)pyrazole |
| 1b-7 | —NH₂ | —CH₃ | 3-methylpyridine-2-carboxylate sodium |
| 1b-8 | —NH₂ | —CH₃ | 2-methylbenzoate sodium |
| 1b-9 | —NH₂ | —CH₃ | 3-methylbenzoate sodium |
| 1b-10 | —NH₂ | —CH₃ | 4-methylbenzoate sodium |
| 1b-11 | —NHCOCH₃ | —CH₃ | 2-methyl-5-sulfonato-benzoate disodium |
| 1b-12 | —NH-(4,6-dihydroxy-1,3,5-triazin-2-yl) | —CH₃ | 2-methyl-5-sulfonato-benzoate disodium |

Identification

Reaction products were identified with a $^{1}H$ and $^{13}C$ nuclear magnetic resonance spectroscope (ECA-400 manufactured by JEOL Ltd.), a high performance liquid chromatograph (LC-20A manufactured by Shimadzu Co.), LC/TOF MS (LC/MSD TOF manufactured by Agilent Technologies), and a UV/Vis spectrophotometer (U-3310 spectrophotometer manufactured by Hitachi, Ltd.)

Inks

A dye compound according to aspects of the present invention may have a brilliant color tone and can have excellent spectral characteristics. Thus, the dye compound can be used as a coloring agent, such as one or more of yellow, magenta, and black, and as a material for recording image information. More specifically, the dye compound can be used as a material (e.g., coloring material) for printing inks, paints, and inks for writing instruments, as well as ink jet inks, as described in detail below.

An example of a method for manufacturing an ink that contains a dye compound according to aspects of the present invention will be described below. In one embodiment, the ink can be used as an ink jet ink. A dye compound having the general formula (1) can be dissolved and/or dispersed in a liquid medium to produce an ink composition for use in inks. For example, the liquid medium may be an aqueous medium. The aqueous medium may be water or a mixed medium of water and a water-soluble organic solvent. Examples of the water-soluble organic solvent may include, but are not limited to, alcohols, polyhydric alcohols, polyglycols, glycol ethers, nitrogen-containing polar solvents, and sulfur-containing polar solvents. The content of the water-soluble organic solvent may be, for example, at least 1% by mass, such as at least 3% by mass of an ink, in view of the moisture retention of the ink, improved solubility of a coloring material, and effective permeation of the ink into a recording paper. The content of the water-soluble organic solvent may also be, for example, not more than 40% by mass, and even not more than 30% by mass. The content of water in an ink may range, for example, from 30% to 95% by mass of the ink. In this range, a coloring material that contains a dye compound according to the present invention may have excellent dispersibility or solubility in the ink. According to aspects of the invention, with this water content, when the ink is used as an ink jet ink, the ink jet printing ink may have a viscosity suitable for stable discharge and cause no clogging at a nozzle tip.

According to one aspect, for an ink jet ink, the amount of the dye compound may range, for example, from 0.2 to 10 parts by mass per 100 parts by mass of the ink, in view of the storage stability of the ink and the graininess of a recorded image. The amount of the dye compound may range, for example, from 0.2 to 5 parts by mass.

An ink that contains a dye compound according to aspects of the present invention may also contain a chemically synthesized surfactant, such as at least one of an ionic surfactant, a nonionic surfactant, and a polymer surfactant. The surfactant may also be derived from a natural product. The derivative may be modified with an enzyme. These surfactants may be used alone or in combination. The total content of surfactants in an ink may range, for example, from 0.5% to 20% by mass of the ink, to maintain high dispersion stability of a dye compound according to aspects of the present invention.

The surfactant may be of any suitable type. Examples of an ionic surfactant include anionic surfactants, such as aliphatic monocarboxylates, polyoxyethylene alkyl ether carboxylates, N-acylsarcosinates, N-acylglutamates, dialkyl sulfosuccinates, alkanesulfonates, alpha-olefin sulfonates, straight chain and branched chain alkylbenzenesulfonates, naphthalenesulfonate-formaldehyde condensates, alkylnaphthalenesulfonates, N-methyl-N-acyltaurinates, alkyl sulfates, polyoxyethylene alkyl ether sulfates, sulfonated oils, alkyl phosphates, polyoxyethylene alkyl ether phosphates, and polyoxyethylene alkylphenyl ether phosphates, cationic surfactants, such as alkylamine salts, alkyltrimethylammonium chlorides, bromides, or iodides, dialkyldimethylammonium chlorides, bromides, or iodides, alkylbenzalkonium chlorides, and alkylpyridinium chlorides, amphoteric surfactants, such as alkylbetaines, fatty acid amide propylbetaines, 2-alkyl-N-carboxymethyl-N-hydroxyethylimidazolinium betaines, alkyl and dialkyl diethylenetriaminoacetic acids, and alkylamine oxides. Examples of a nonionic surfactant include glycerin fatty acid esters, sorbitan fatty acid esters, sucrose fatty acid esters, polyoxyethylene alkyl ethers, polyoxyethylene alkylphenyl ethers, polyoxyethylenepolyoxypropylene glycols, fatty acid polyethylene glycols, fatty acid polyoxyethylene sorbitans, and fatty acid alkanolamides.

Examples of a polymer surfactant include anionic polymers, such as polyacrylates, styrene-acrylate copolymers, vinylnaphthalene-acrylate copolymers, styrene-maleate copolymers, vinylnaphthalene-maleate copolymers, and polyphosphoric acids, and nonionic polymers, such as poly(vinyl alcohol), polyvinylpyrrolidone, and polyalkylene glycols.

Surfactants derived from natural products and their enzyme-modified surfactants include proteins, such as gelatin and casein, natural rubbers, such as gum arabic, glycosides, such as saponin, cellulose derivatives, such as alkylcellulose, carboxyalkylcellulose, and hydroxyalkylcellulose, natural polymers, such as lignin sulfonate and shellac, and food surfactants, such as lecithin and lysolecithin.

The pH of ink in the production of the ink using a dye compound according to aspects of the present invention may be, for example, in the range of 4.0 to 11.0, in view of the handleability of the ink, but is not limited thereto. In the production of an ink jet ink, the ink may also contain a moisture-retentive solid component, such as at least one of urea, a urea derivative, and trimethylolpropane, to retain the moisture in the ink. The content of the moisture-retentive solid component, such as at least one of urea, a urea derivative, and trimethylolpropane in the ink may be, for example, at least 0.1% by mass, and even at least 3.0% by mass, and not more than 20.0% by mass, such as not more than 10.0% by mass of the ink.

The ink may also optionally contain various additives, such as at least one of a pH adjuster, an anticorrosive, a preservative, a fungicide, an antioxidant, a reduction inhibitor, an evaporation accelerator, a chelator, and a water-soluble polymer.

An ink that is produced using a dye compound according to aspects of the present invention may be suitable for an ink jet recording method, such as for example a method which discharges droplets by the action of thermal energy. An ink according to aspects of the present invention may also be used in another ink jet recording method, and as a material for general writing instruments. A dye compound according to aspects of the present invention can be used not only as a coloring agent, but also for example as an electronic material, such as a dye for use in optical recording or color filters.

EXAMPLES

The present invention will be described in detail below by way of examples and comparative examples. However, the present invention is not limited to these examples. Unless otherwise specified, "parts" and "%" are based on mass.

Example 1

A dye compound (1a-1), which is a specific example of a dye compound having the general formula (1), was produced as follows.

Synthesis Example 1

In Synthesis Example 1, a compound (7) was produced as follows.

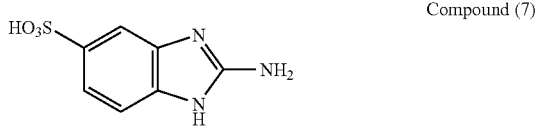

Compound (7)

Five grams of 2-aminobenzimidazole was completely dissolved in 10 g of 20% fuming sulfuric acid. The solution was heated at 100° C. for six hours. The solution was then cooled and slowly added dropwise to 50 g of ice water. Precipitated crystals were filtered off and washed sufficiently with ethanol. The crystals were dried to yield 7.6 g of compound (7) as a powder.

Synthesis Example 2

In Synthesis Example 2, a compound (8) was produced as follows.

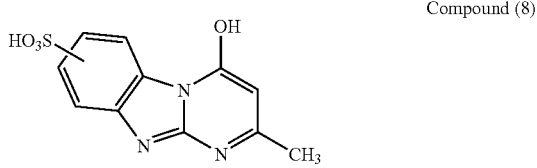

Compound (8)

7.6 g of compound (7), 30 g of ethyl acetoacetate, and 13 g of N,N-dimethylaniline were reacted at 150° C. for four hours with stirring. The resulting product was cooled and poured into 100 mL of ethanol. Precipitated crystals were filtered off and washed sufficiently with ethanol. The crystals were dried to yield 7.4 g of compound (8) as a white powder. $^1$H NMR analysis showed that the white powder was a 56%/44% mixture of two structural isomers in which the substitution positions of a sulfonic acid group were different.

Synthesis Example 3

In Synthesis Example 3, a dye compound (1a-1) having the following structure was produced.

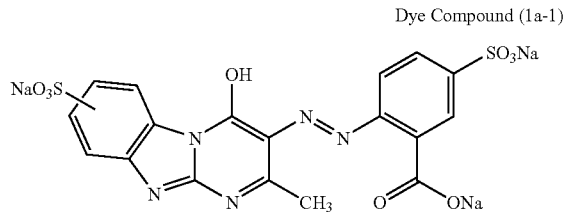

Dye Compound (1a-1)

5.7 g of 5-sulfoanthranilic acid and 0.95 g of 35% hydrochloric acid solution were added to 100 mL of water and were cooled to 5° C. or less with stirring. 1.8 g of sodium nitrite was added to the solution. After the solution was stirred for one hour, residual sodium nitrite was decomposed with 0.77 g of amidosulfuric acid to yield a diazotization solution. 7.4 g of white powder of the compound (8) produced in Synthesis Example 2 and 10 g of sodium hydrogencarbonate were added to 100 mL of water and were cooled to 5° C. or less with stirring. The diazotization solution was slowly added dropwise to the suspension containing the compound (8). The suspension was stirred for eight hours. The aqueous solution was then desalinated by electrodialysis and was dried to yield 12 g of dye compound (1a-1) as a yellow powder. $^1$H NMR analysis showed that the yellow powder was a 56%/44% mixture of two structural isomers in which the substitution positions of a sulfonic acid group were different. NMR analysis, mass spectrometry, HPLC analysis, and UV/Vis spectroscopic analysis using the apparatuses and conditions described above showed that the dye compound (1a-1) had the structure described above. The following are results of the analyses.

Results of Analyses of Dye Compound (1a-1)

Figure 2:
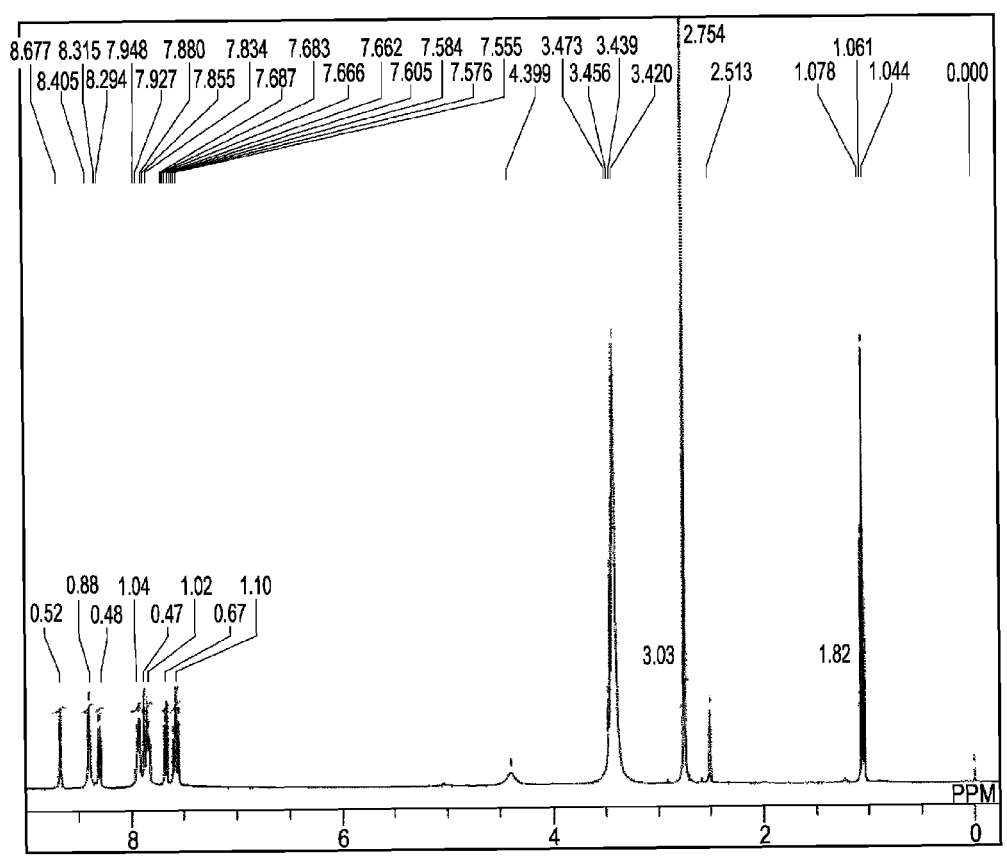
FIG. 2 shows a $^1$H NMR spectrum of a dye compound (1a-1) according to an embodiment of the present invention in DMSO-$d_6$ at 23° C. at 400 MHz.

[1] Result of $^1$H NMR (400 MHz, DMSO-$d_6$, 23° C.) [FIG. 2]:

δ [ppm]=2.75 (s, 3H), 7.58 (d, 1H), 7.67 (d, 0.56H), 7.84 (d, 0.44H), 7.85 (d, 0.56H), 7.88 (d, 0.44H), 7.93 (dd, 1H), 8.30 (d, 0.44H), 8.41 (d, 1H), and 8.68 (d, 0.56H)

[2] Result of Mass Spectrometry (ESI-TOF):

m/z=549.97 (M-Na)$^-$, 263.49 (M-2Na)$^{2-}$, 168.00 (M-3Na)$^{3-}$

[3] Result of HPLC:

Purity=97.0% by area, retention time 11.6 min (35.4% by area), and retention time 11.9 min (61.6% by area) (0.1 mM TFA solution-MeOH)

[4] Result of UV/Vis Spectroscopic Analysis [FIG. 1]:

$\lambda_{max}$=452.0 nm, $\epsilon$=32462 M$^{-1}$cm$^{-1}$ (solvent: H$_2$O, 23° C.)

Example 2

Preparation Example of Ink 1

A hundred parts of the following components in total were sufficiently dissolved with stirring to produce an ink (A).

3.5 parts of dye compound (1a-1)

One part of Acetylenol EH (trade name, manufactured by Kawaken Fine Chemicals Co., Ltd.), which is an ethylene oxide adduct of acetylene glycol 7.5 parts of ethylene glycol 7.5 parts of glycerin 7.5 parts of urea Ion-exchanged water as the remainder

Preparation Examples of Inks 2 to 7

Inks (B) to (G) were produced in the same manner as Preparation Example of Ink 1 except that the dye compound (1a-1) used in Preparation Example of Ink 1 was replaced by a dye compound (1a-6), dye compounds (1a-9) to (1a-11), a dye compound (1b-1), or a dye compound (1b-11).

Comparative Preparation Examples of Inks 1 to 4

Comparative inks (H) to (K) were produced in the same manner as Preparation Example of Ink 1 except that the dye compound (1a-1) used in Preparation Example of Ink 1 was replaced by the following comparative dye compounds (9) to (12).

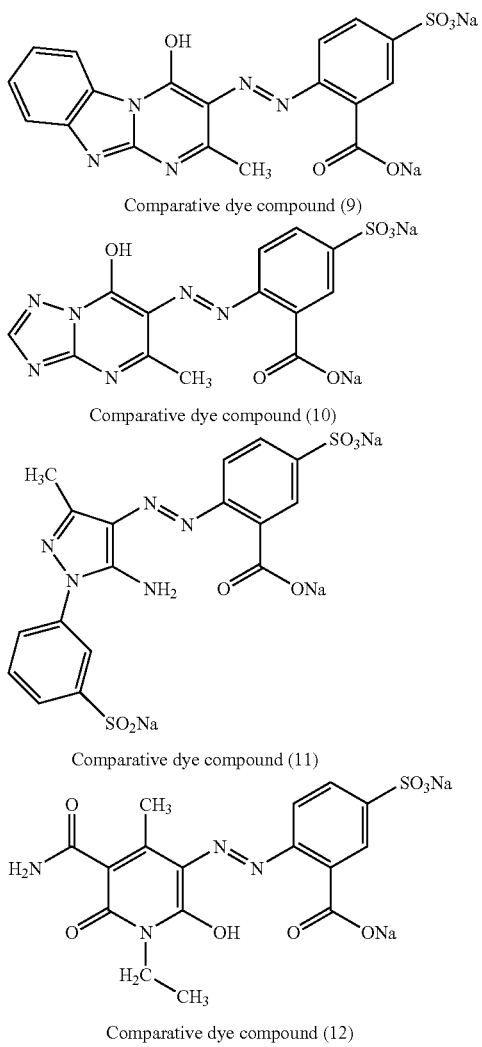

Comparative dye compound (9)

Comparative dye compound (10)

Comparative dye compound (11)

Comparative dye compound (12)

FIG. 1 shows ultraviolet-visible absorption spectra of the dye compound (1a-1) and the comparative dye compound (11) in water at room temperature.

Evaluations

The inks (A) to (G) produced in Preparation Examples of Inks 1 to 7 and the comparative inks (H) to (K) produced in Comparative Preparation Examples of Inks 1 to 4 were charged in an ink cartridge of an ink jet printer Pixus iP8600 manufactured by CANON KABUSHIKI KAISHA. A solid image with two-centimeter sides was printed with the ink jet printer on a professional photo paper (PR-101) manufactured by CANON KABUSHIKI KAISHA. The photo paper was naturally dried for 24 hours and was used for evaluation.

Light Resistance

The photo paper was placed in an Atlas weatherometer (Ci4000 manufactured by Toyo Seiki Seisaku-Sho, Ltd.) for 50 hours. The conditions were as follows: black panel temperature 50° C., chamber temperature 40° C., relative humidity 70%, and irradiance (340 nm) 0.39 W/m². The photo paper was evaluated with SpectroLino (Gretag Macbeth AG). The optical density and chromaticity (L*, a*, and b*) in the L*a*b* color system were measured. The color difference (ΔE) was calculated from measured chromaticity values by the following equation.

Color difference($\Delta E$)=$\sqrt{\{(a^*(\text{before test})-a^*(\text{after test}))^2+(b^*(\text{before test})-b^*(\text{after test}))^2+(L^*(\text{before test})-L^*(\text{after test}))^2\}}$ The evaluation criteria were as follows:
Good: ΔE was less than 5.
Fair: ΔE was 5 or more but less than 10.
Poor: ΔE was 10 or more.

Gas Resistance

The photo paper was placed in an ozone weather meter (OMS-H manufactured by Suga Test Instruments Co., Ltd.) at an ozone concentration of 10 ppm, a temperature of 24° C., and a relative humidity of 60% for four hours. The reflection density of the photo paper was measured before and after the exposure. The results were evaluated on the basis of the same criteria as in light resistance. The color difference (ΔE) was calculated from measured chromaticity values by the following equation.

Color difference($\Delta E$)=$\sqrt{\{(a^*(\text{before test})-a^*(\text{after test}))^2+(b^*(\text{before test})-b^*(\text{after test}))^2+(L^*(\text{before test})-L^*(\text{after test}))^2\}}$ The evaluation criteria were as follows:
Good: ΔE was less than 5.
Fair: ΔE was 5 or more but less than 10.
Poor: ΔE was 10 or more.

Storage Stability

The inks (A) to (G) produced in Preparation Examples of Inks 1 to 7 and the comparative inks (H) to (K) produced in Comparative Preparation Examples of Inks 1 to 4 were placed in an airtight glass container and were left stand at 60° C. for one month. The absorbance (Abs) was then measured at a maximum absorption wavelength by UV/Vis spectroscopic analysis and was compared with the absorbance measured before the test ($Abs_0$).

The evaluation criteria were as follows:
Good: $Abs/Abs_0$ was 0.95 or more.
Fair: $Abs/Abs_0$ was 0.90 or more but less than 0.95.
Poor: $Abs/Abs_0$ was less than 0.90.

Table 3 shows the type of dye used in inks and the results of light resistance, gas resistance, and storage stability.

TABLE 3

| Ink | Compound No. | Light resistance | Gas resistance | Storage stability |
|---|---|---|---|---|
| (A) | Dye compound (1a-1) | ⊚ | ⊚ | ⊚ |
| (B) | Dye compound (1a-6) | ⊚ | ⊚ | ⊚ |
| (C) | Dye compound (1a-9) | ⊚ | ⊚ | ⊚ |
| (D) | Dye compound (1a-10) | ⊚ | ○ | ⊚ |
| (E) | Dye compound (1a-11) | ⊚ | ○ | ⊚ |
| (F) | Dye compound (1b-1) | ⊚ | ⊚ | ⊚ |
| (G) | Dye compound (1b-11) | ⊚ | ⊚ | ⊚ |
| (H) | Comparative dye compound (9) | X | ○ | ⊚ |
| (I) | Comparative dye compound (10) | ○ | ○ | X |
| (J) | Comparative dye compound (11) | X | X | ⊚ |
| (K) | Comparative dye compound (12) | X | ○ | ⊚ |

Table 3 shows that inks containing a dye compound according to the present invention had relatively high light resistance, gas resistance, and storage stability, indicating that the dye compounds are useful for inks.

Thus, the dye compounds of the examples in accordance with aspects of the invention may have excellent weatherability, such as light resistance and gas resistance. Furthermore, the dye compounds of the examples, when used as a coloring material for an ink, such as an ink jet ink, may be capable of forming images having high storage stability, as well as relatively high light resistance and gas resistance.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Patent Application No. 2008-118803 filed Apr. 30, 2008, which is hereby incorporated by reference herein in its entirety.

What is claimed is:

1. A dye compound having the following general formula (1):

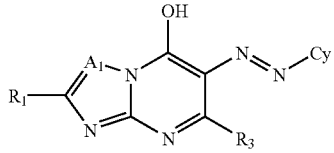

General Formula (1)

wherein in general formula (1), $A_1$ denotes N or $CR_2$, wherein when $A_1$ denotes N, $R_1$ denotes an amino group, and when $A_1$ denotes $CR_2$, $R_1$ and $R_2$ form an aromatic ring that has an anionic group, $R_3$ denotes an alkyl group, an aryl group, or an aralkyl group, and Cy denotes a substituted or unsubstituted aromatic ring.

2. The dye compound according to claim 1, wherein the dye compound having the general formula (1) is a dye compound having the following general formula (2):

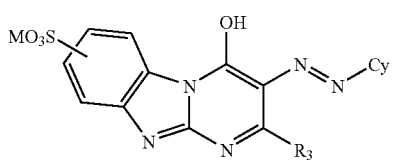

General Formula (2)

wherein in general formula (2), $R_3$ denotes an alkyl group, an aryl group, or an aralkyl group, Cy denotes a substituted or unsubstituted aromatic ring, and M denotes a hydrogen atom or a counter ion.

3. The dye compound according to claim 1, wherein Cy in the general formula (1) is an aromatic ring substituted with a carboxylic acid group or a sulfonic acid group.

4. The dye compound according to claim 1, wherein Cy in the general formula (1) is an aromatic ring that has a carboxylic acid group or a sulfonic acid group adjacent to an azo group.

5. The dye compound according to claim 1, wherein Cy in the general formula (1) is a nitrogen-containing heteroaromatic ring.

6. The dye compound according to claim 1, wherein Cy in the general formula (1) is a five-membered nitrogen-containing heteroaromatic ring.

7. An ink comprising the dye compound according to claim 1 and an aqueous medium.

8. The ink according to claim 7, wherein the ink is an ink jet ink.

\* \* \* \* \*